(12) United States Patent
Chen et al.

(10) Patent No.: US 8,759,543 B2
(45) Date of Patent: Jun. 24, 2014

(54) BITHIOPHENE DERIVATIVES AND SEMICONDUCTOR DEVICES COMPRISING THE SAME

(75) Inventors: Liang-Hsiang Chen, Taichung (TW); Ming-Chou Chen, Hsinchu County (TW); Chia-Ming Yeh, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 240 days.

(21) Appl. No.: 13/462,009

(22) Filed: May 2, 2012

(65) Prior Publication Data

US 2013/0168642 A1 Jul. 4, 2013

(30) Foreign Application Priority Data

Jan. 2, 2012 (TW) .............................. 101100021 A

(51) Int. Cl.
*C07D 333/34* (2006.01)
(52) U.S. Cl.
CPC .................................. *C07D 333/34* (2013.01)
USPC .......................................................... 549/42
(58) Field of Classification Search
CPC ...................................................... C07D 333/34
USPC .......................................................... 549/42
See application file for complete search history.

(56) References Cited

U.S. PATENT DOCUMENTS

| | | | |
|---|---|---|---|
| 6,998,068 | B2 | 2/2006 | Gerlach |
| 7,109,519 | B2 | 9/2006 | Gerlach |
| 7,368,510 | B2 | 5/2008 | Lee et al. |
| 7,582,897 | B2 | 9/2009 | Hirai et al. |
| 7,585,933 | B2 | 9/2009 | Motohiro et al. |
| 7,601,279 | B2 | 10/2009 | Masuda |
| 2008/0076935 | A1 | 3/2008 | Nishikawa et al. |

FOREIGN PATENT DOCUMENTS

| | | |
|---|---|---|
| CN | 1807428 A | 7/2006 |
| CN | 1835941 A | 9/2006 |
| CN | 1891732 A | 1/2007 |
| TW | 201001773 A1 | 1/2010 |
| WO | 2011/102390 A1 | 8/2011 |

OTHER PUBLICATIONS

Ahmed et al., "Thieno[3,2-b]thiophene oligomers and their applications as p-type organic semiconductors", Journal of Materials Chemistry, 2009, 19, pp. 3449-3456.
Kanazawa et al., "The effect of thiophene sequence separation on air-stable organic thin-film transistor materials", Organic Electronics, 2008, 9, pp. 425-431.
Kumagai et al., "Effect of the Substitution Pattern of Alkyl Side Chain in a Benzodithiophene Core • -System on Intra and Inter-Molecular Charge Carrier Mobility", The Journal of Physical Chemistry B, 2011, 115, pp. 8446-8452.
Shinamura et al., "Synthesis, Properties, Crystal Structures, and Semiconductor Characteristics of Naphtho[1,2-b:5,6-b'] dithiophene and -diselenophene Derivatives", J. Org. Chem., 2010, vol. 75, No. 4, pp. 1228-1234.
Sista el al., "Enhancement of OFET Performance of Semiconducting Polymers Containing Benzodithiophene Upon Surface Treatment with Organic Silanes", Journal of Polymer Science Part A: Polymer Chemistry, 2011, vol. 49, pp. 2292-2302.
Tang et al., "Pentaceno[2,3-b]thiophene, a Hexacene Analogue for Organic Thin Film Transistors", J. Am. Chem. Soc., 2009,131, pp. 882-883.
Taiwan Office Action for Appl. No. 201210041694.4 dated Feb. 12, 2014.
Chinese Office Action for Appl. No. 201210041694.4 dated Feb. 12, 2014.

*Primary Examiner* — Taofiq A Solola
(74) *Attorney, Agent, or Firm* — Birch, Stewart, Kolasch & Birch, LLP

(57) ABSTRACT

In an embodiment of the disclosure, a bithiophene derivative is provided. The bithiophene derivative has formula (I):

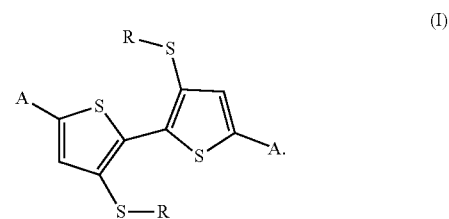

In formula (I), R is C8-25 alkyl, and A includes

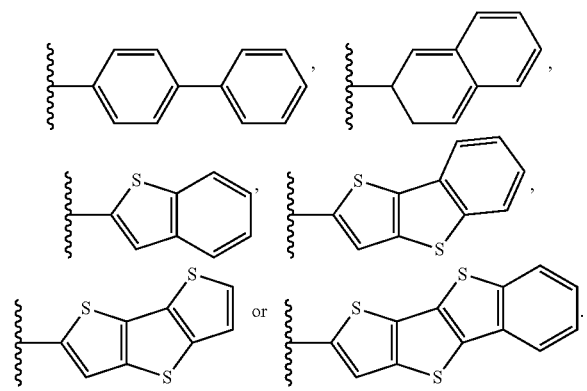

In another embodiment of the disclosure, a semiconductor device including the bithiophene derivative is further provided.

5 Claims, 7 Drawing Sheets

BITHIOPHENE DERIVATIVES AND SEMICONDUCTOR DEVICES COMPRISING THE SAME

CROSS REFERENCE TO RELATED APPLICATIONS

This application claims priority of Taiwan Patent Application No. 101100021, filed on Jan. 2, 2012, the entirety of which is incorporated by reference herein.

BACKGROUND OF THE DISCLOSURE

1. Field of the Disclosure

The disclosure relates to an organic semiconductor, and more particularly to a soluble bithiophene derivative.

2. Description of the Related Art

For organic semiconductor materials, the most popular material used as the material of the active layer is pentacyclic molecule materials; however, it could be oxidization in air through time and causes electrical performance of devices made therefrom to decline through time. Therefore, development of novel organic semiconductor materials is desirable.

BRIEF SUMMARY OF THE DISCLOSURE

One embodiment of the disclosure provides a bithiophene derivative of formula (I):

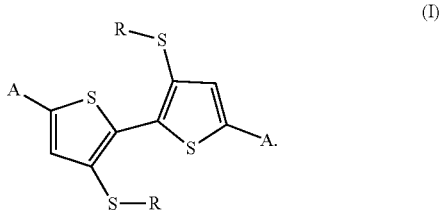

In formula (I), R is C8-25 alkyl; and A comprises

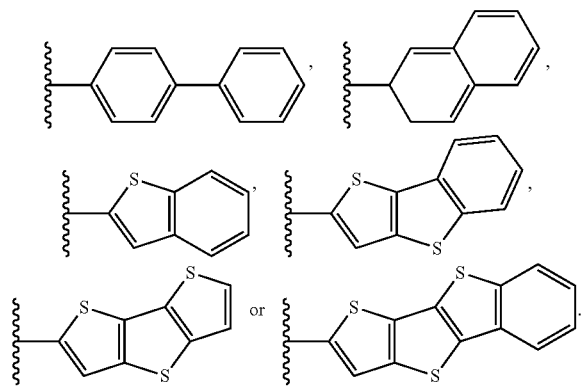

One embodiment of the disclosure provides a semiconductor device, comprising: a substrate; a gate electrode formed on the substrate; an insulation layer formed on the gate electrode and the substrate; a source and a drain formed on the insulation layer; and a semiconductor layer formed on the insulation layer, the source and the drain, wherein the semiconductor layer comprises the disclosed bithiophene derivative of formula (I).

For the novel organic semiconductor material provided by the disclosure, various conjugate systems extended from the bithiophene act as the core structure of the material efficiently improving the electrical performance of the material. The long alkyl chains connected to the bithiophene facilitate the dissolving of the material in common solvents so that the material can be applied a liquid-liquid low-temperature process to proceed with large-area fabrication through, for example, the method of coating, which lowers the costs of devices manufactured therefrom and increases the convenience of manufacturing procedures. Additionally, the sulfur atoms are conducted into the molecule structure of the material, advancing the regularity of molecular arrangements and the solubility of the material through the strong interaction force between the sulfur atoms and Van der Waals force formed between the long alkyl chains. Therefore, the disclosure provides a soluble organic semiconductor containing bithiophene which has excellent material characteristics of, for example, high carrier mobility, high stability (difficult to oxidize in air) and simple fabrication steps.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawing, wherein.

DETAILED DESCRIPTION OF THE DISCLOSURE

Figure 1:
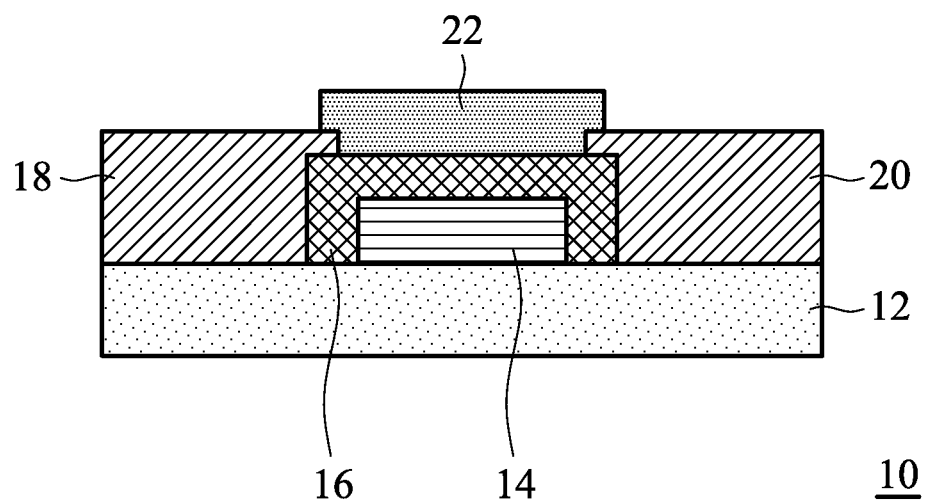
FIG. 1 shows a cross-sectional view of a semiconductor device according to an embodiment of the disclosure.
Figure 2:
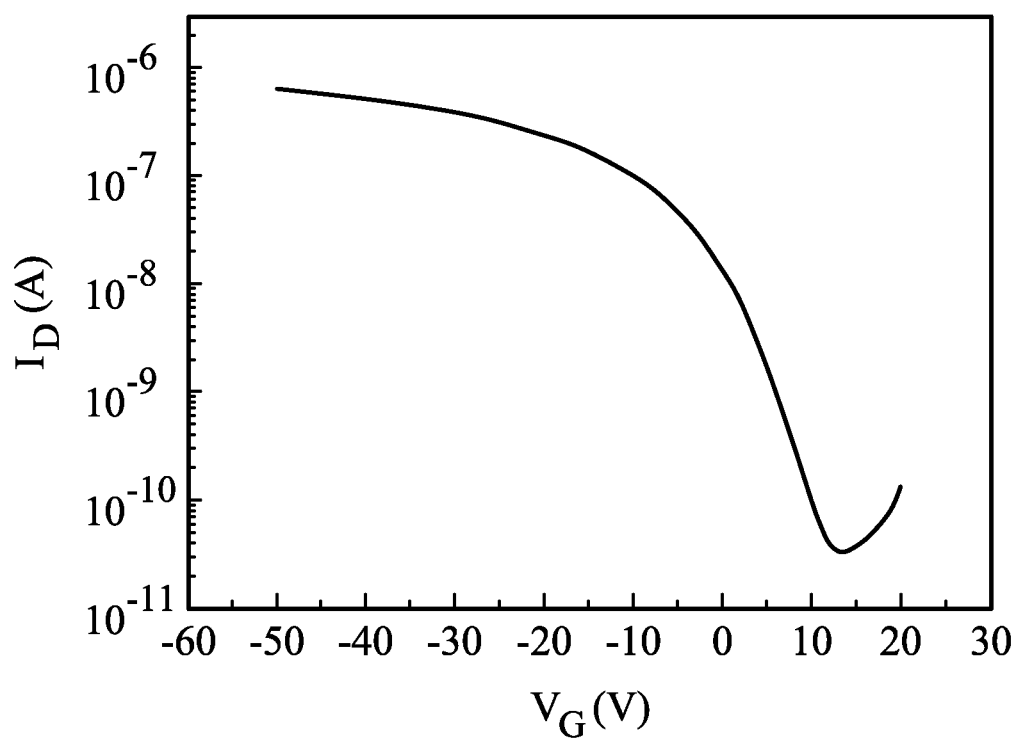
FIG. 2 shows $I_D$-$V_G$ relationship of semiconductor device I according to an embodiment of the disclosure.
Figure 3:
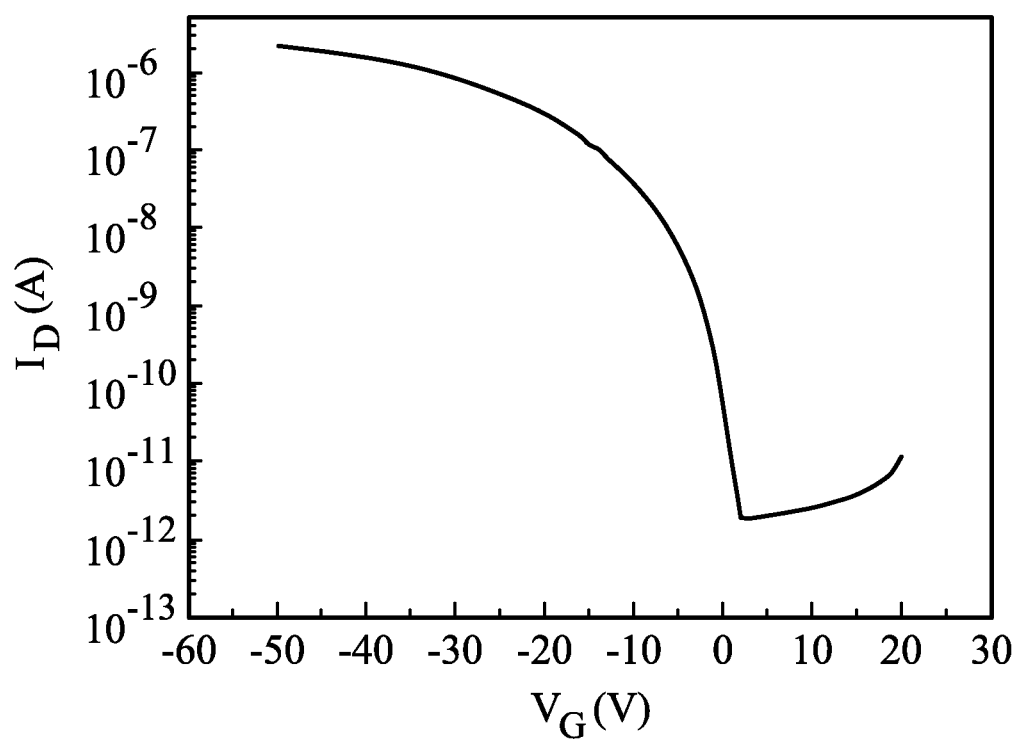
FIG. 3 shows $I_D$-$V_G$ relationship of semiconductor device II according to an embodiment of the disclosure.
Figure 4:
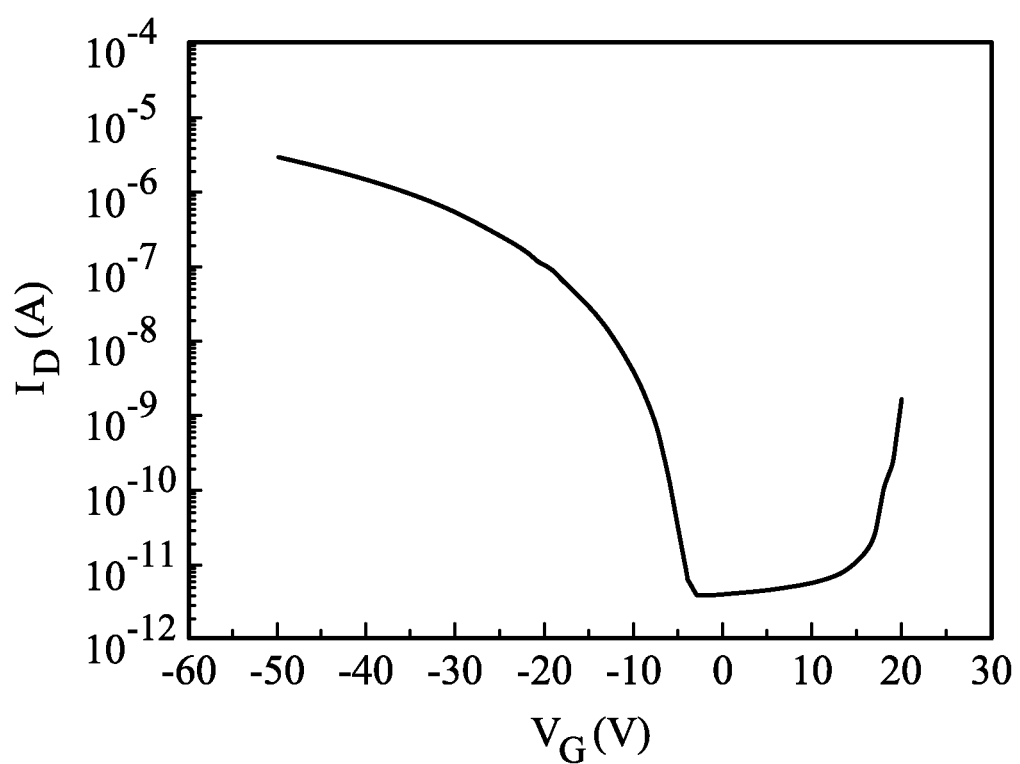
FIG. 4 shows $I_D$-$V_G$ relationship of semiconductor device III according to an embodiment of the disclosure.
Figure 5:
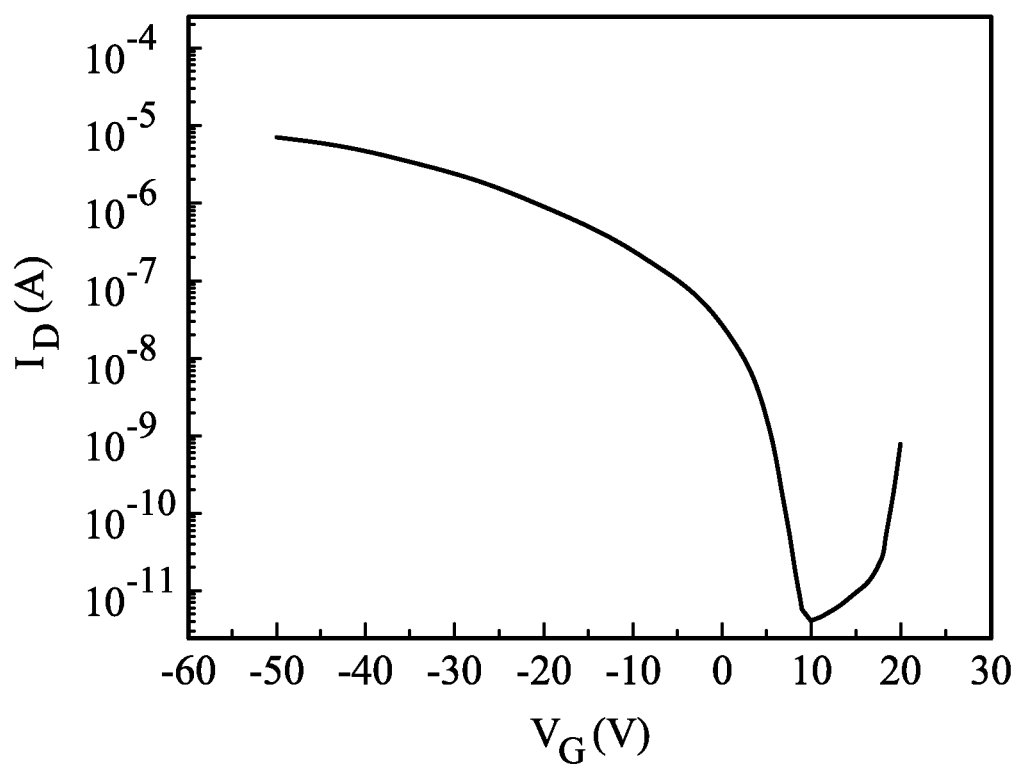
FIG. 5 shows $I_D$-$V_G$ relationship of semiconductor device IV according to an embodiment of the disclosure.
Figure 6:
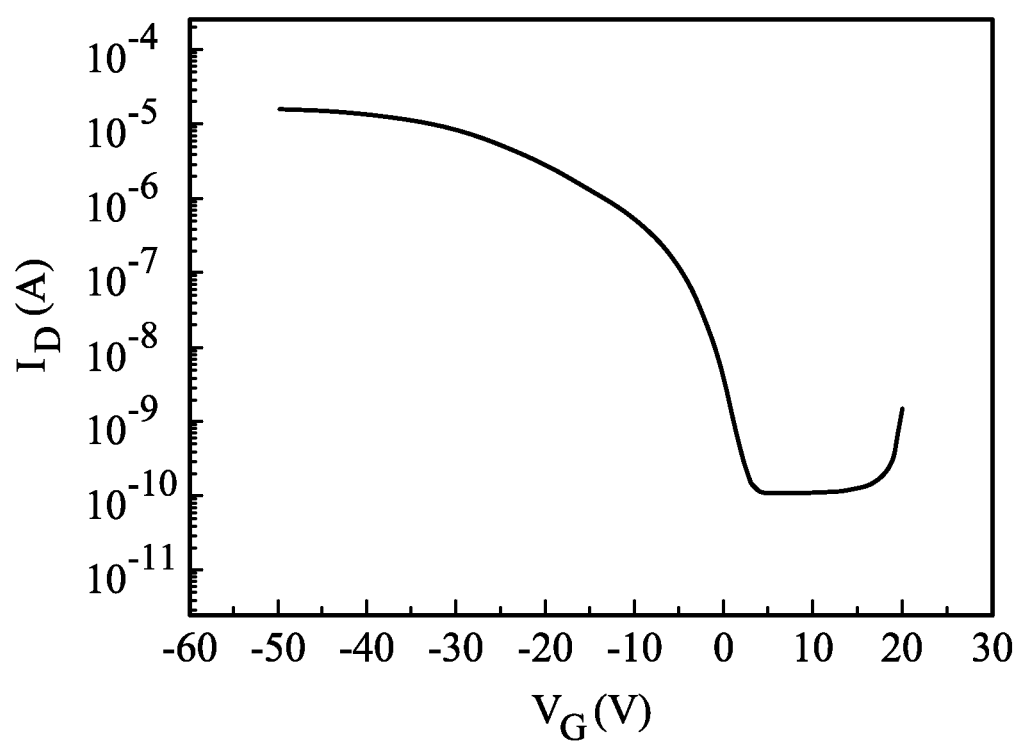
FIG. 6 shows $I_D$-$V_G$ relationship of semiconductor device V according to an embodiment of the disclosure.
Figure 7:
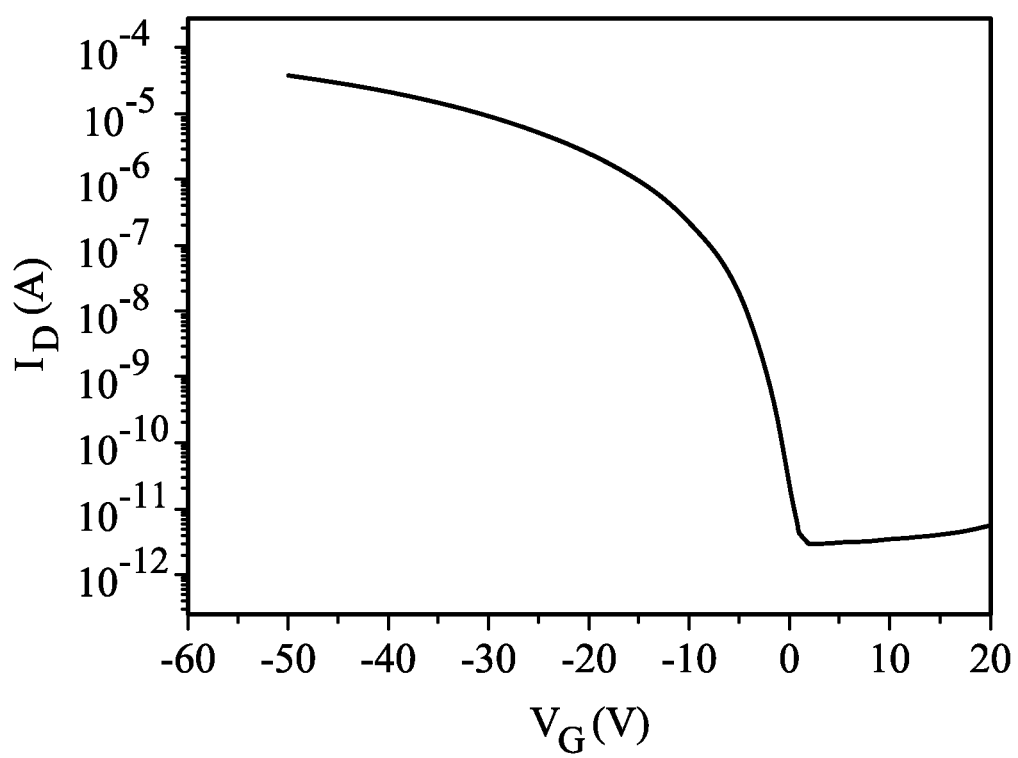
FIG. 7 shows $I_D$-$V_G$ relationship of semiconductor device VI according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One embodiment of the disclosure provides a bithiophene derivative of formula (I):

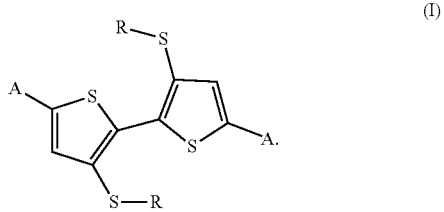

In formula (I), R may be C8-25 alkyl. A may comprise

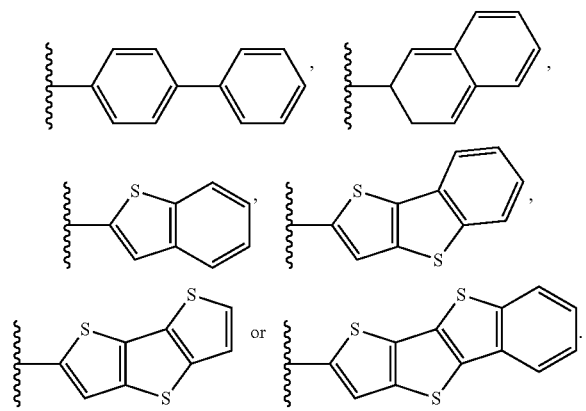

Exemplary bithiophene derivatives of the disclosure are shown as follows.

(Compound DBP-BST)

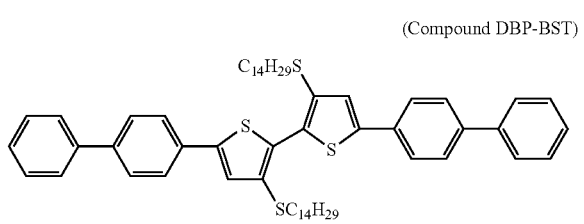

(Compound DNp-BST)

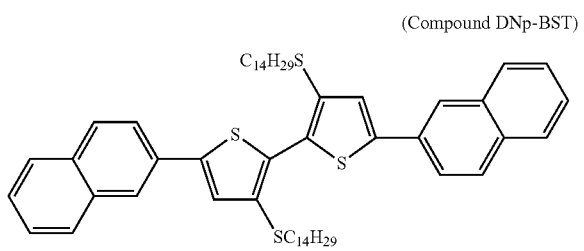

(Compound DBT-BST)

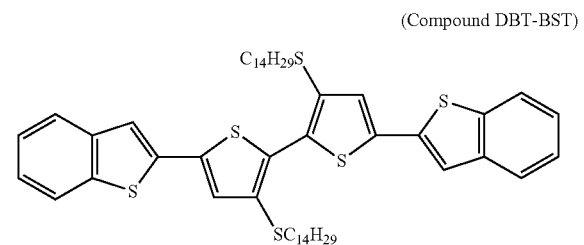

(Compound DBTT-BST)

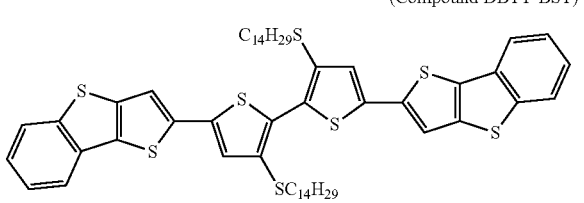

(Compound DDTT-BST)

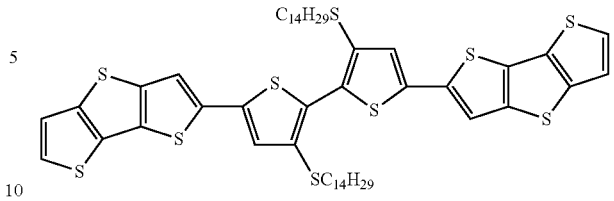

(Compound DBTDT-BST)

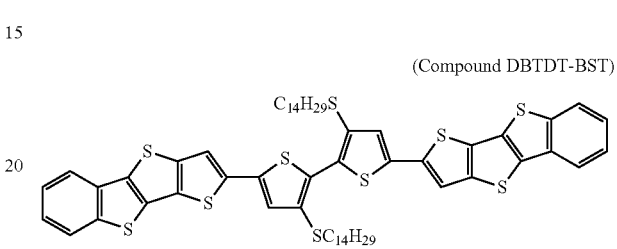

Referring to FIG. 1, in accordance with one embodiment of the disclosure, a semiconductor device is provided. A semiconductor device 10 comprises a substrate 12, a gate electrode 14, an insulation layer 16, a source 18, a drain 20 and a semiconductor layer 22. The gate electrode 14 is formed on the substrate 12. The insulation layer 16 is formed on the gate electrode 14 and the substrate 12. The source 18 and the drain 20 are formed on the insulation layer 16. The semiconductor layer 22 is formed on the insulation layer 16, the source 18 and the drain 20. Specifically, the semiconductor layer 22 comprises the disclosed bithiophene derivative of formula (I). The substrate 12 may comprise glass substrate, quartz substrate, silicon wafer, plastic substrate or metal film. The gate electrode 14, the source 18 and the drain 20 may comprise metal such as tantalum alloy, silver alloy, copper alloy, aluminum alloy or molybdenum alloy, or conductive polymers. The insulation layer 16 may comprise any proper organic or inorganic insulation material. In this embodiment, the semiconductor device 10 is a bottom gate device. However, the disclosure is not limited thereto. The disclosed bithiophene derivative of formula (I) may be also applied to a semiconductor layer between a gate electrode and a source/drain of a top gate device.

For the novel organic semiconductor material provided by the disclosure, various conjugate systems extended from the bithiophene act as the core structure of the material efficiently improving the electrical performance of the material. The long alkyl chains connected to the bithiophene facilitate the dissolving of the material in common solvents so that the material can be applied a liquid-liquid low-temperature process to proceed with large-area fabrication through, for example, the method of coating, which lowers the costs of devices manufactured therefrom and increases the convenience of manufacturing procedures. Additionally, the sulfur atoms are conducted into the molecule structure of the material, advancing the regularity of molecular arrangements and the solubility of the material through the strong interaction force between the sulfur atoms and Van der Waals force formed between the long alkyl chains. Therefore, the disclosure provides a soluble organic semiconductor containing bithiophene which has excellent material characteristics of, for example, high carrier mobility, high stability (difficult to oxidize in air) and simple fabrication steps.

Example 1

Synthesis of the Bithiophene Derivative I (Compound DBP-BST)

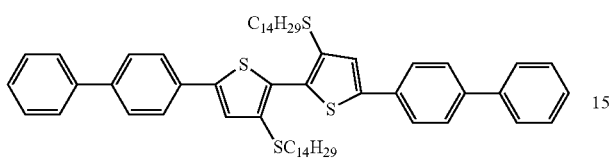

Synthesis Scheme:

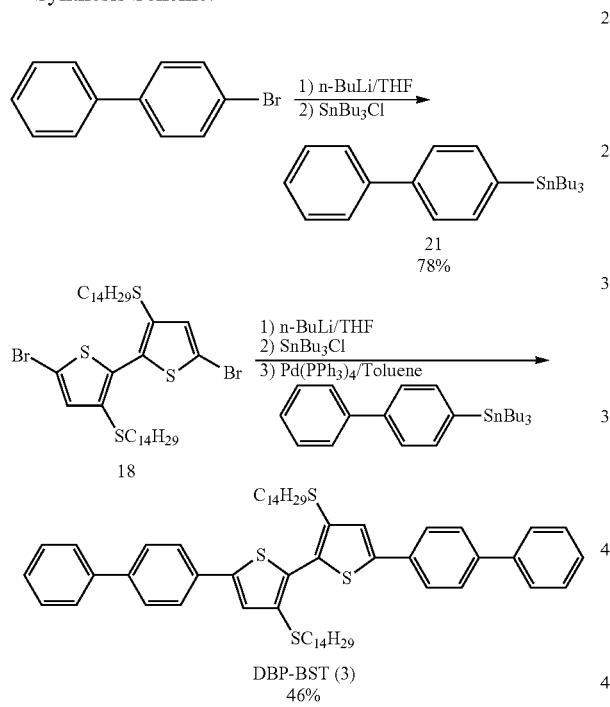

(1) Synthesis of 4-tributylstannylbiphenyl 21

2.5 M of n-BuLi (2.1 mL/hexane, 5.32 mmol) was added to 4-bromobiphenyl (1.24 g, 5.32 mmol/THF (20 mL)) and reacted at −78° C. for 40 minutes under a dry and anaerobic operation condition to form a solution. SnBu$_3$Cl (1.65 mL, 5.85 mmol) was then added to the solution and reacted at −78° C. for 1 hour. After returning to room temperature, the solution was continuously reacted for 8 hours. After the reaction was completed, the solution was extracted by ether (30 mL) and deionized water (50 mL). An organic phase was collected. After removal of ether by a rotary concentrator, the organic phase was purified by reduced-pressure distillation to form a transparent colorless oily product (21, 1.83 g, 78%).

(2) Synthesis of 5,5'-di(4-biphenyl)-3,3'-bis(tetradecanylsulfanyl)-2,2'-bithiophene (DBP-BST) 3

4-tributylstannylbiphenyl 21 (0.25 g, 0.56 mmol) was added to diBr-BST 18 (0.2 g, 0.26 mmol)/Pd(PPh$_3$)$_4$ (12 mg, 0.01 mmol)/toluene (30 mL)) and reacted with thermal reflux at 140° C. for 2 days under a dry and anaerobic operation condition to form a solution. After the reaction was completed, the solution was spun to remove toluene. The solution was then purified by column chromatography using hexane as an elution solution and recrystallized to obtain an orange solid (3, 110 mg, 46%).

$^1$H NMR (300 MHz, CDCl$_3$): δ 7.7 (d, J=7.8 Hz, 4H), 7.64 (d, J=7.8 Hz, 8H), 7.47 (t, J=7.5 Hz, 2H), 7.37 (d, J=7.2 Hz, 4H), 7.35 (s, 2H), 2.88 (t, J=7.2 Hz, 4H), 1.61 (m, 4H), 1.37 (m, 4H), 1.22 (m, 40H), 0.86 (t, J=6.6 Hz, 6H).

Example 2

Synthesis of the Bithiophene Derivative II (Compound DNp-BST)

Synthesis Scheme:

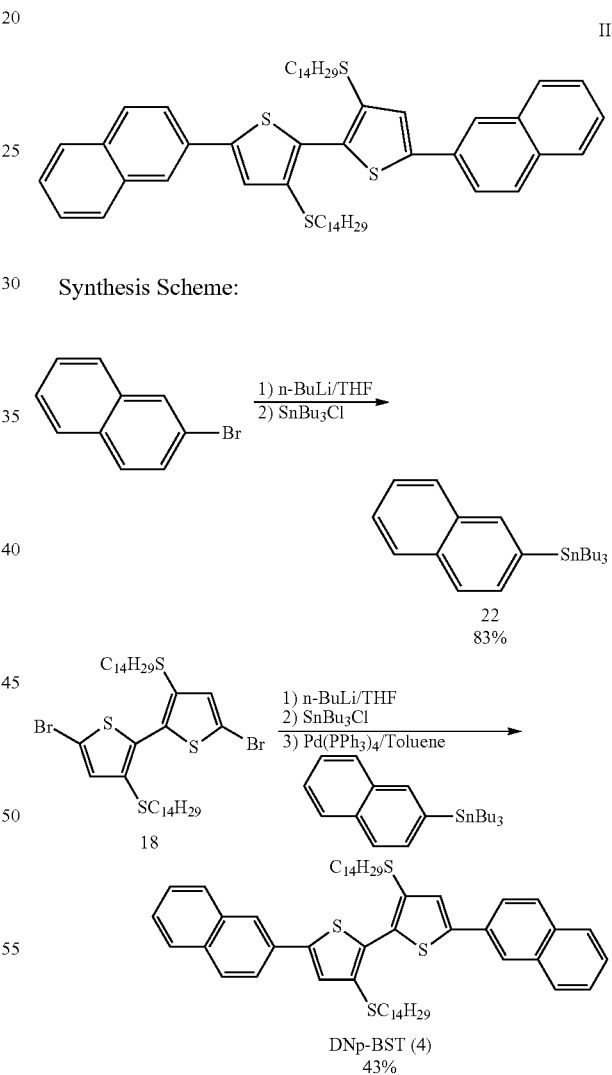

(1) Synthesis of 2-tributylstannylnaphthalene 22

2.5 M of n-BuLi (1.9 mL/hexane, 4.83 mmol) was added to 2-bromonaphthalene (1 g, 4.83 mmol/THF (20 mL)) and reacted at −78° C. for 40 minutes under a dry and anaerobic operation condition to form a solution. SnBu₃Cl (1.5 mL, 5.31 mmol) was then added to the solution and reacted at −78° C. for 1 hour. After returning to room temperature, the solution was continuously reacted for 8 hours. After the reaction was completed, the solution was extracted by ether (30 mL) and deionized water (50 mL). An organic phase was collected. After removal of ether by a rotary concentrator, the organic phase was purified by reduced-pressure distillation to form a transparent pale yellow oily product (22, 1.68 g, 83%).

(2) Synthesis of 5,5'-di(naphthalen-2-yl)-3,3'-bis(tetradecanylsulfanyl)-2,2'-bithiophene (DNp-BST) 4

4-tributylstannylnaphthalene 22 (0.24 g, 0.56 mmol) was added to diBr-BST 18 (0.2 g, 0.26 mmol/Pd(PPh₃)₄ (12 mg, 0.01 mmol)/toluene (30 mL)) and reacted with thermal reflux at 140° C. for 2 days under a dry and anaerobic operation condition to form a solution. After the reaction was completed, the solution was spun to remove toluene. The solution was then purified by column chromatography using hexane as an elution solution and recrystallized to obtain an orange solid (4, 100 mg, 43%).

¹H NMR (300 MHz, CDCl₃): δ 8.07 (s, 2H), 7.89-7.82 (m, 6H), 7.75 (dd, J=7.8 Hz, J=1.8 Hz, 2H), 7.52-7.47 (m, 4H), 7.45 (s, 2H), 2.92 (t, J=7.2 Hz, 4H), 1.64 (m, 4H), 1.39 (m, 4H), 1.12 (m, 40H), 0.87 (t, J=6.9 Hz, 6H).

Example 3

Synthesis of the Bithiophene Derivative III
(Compound DBT-BST)

III

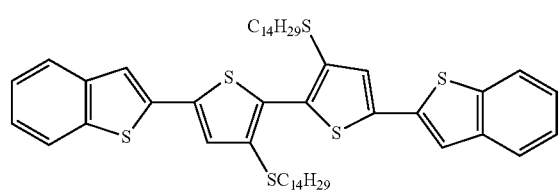

Synthesis Scheme:

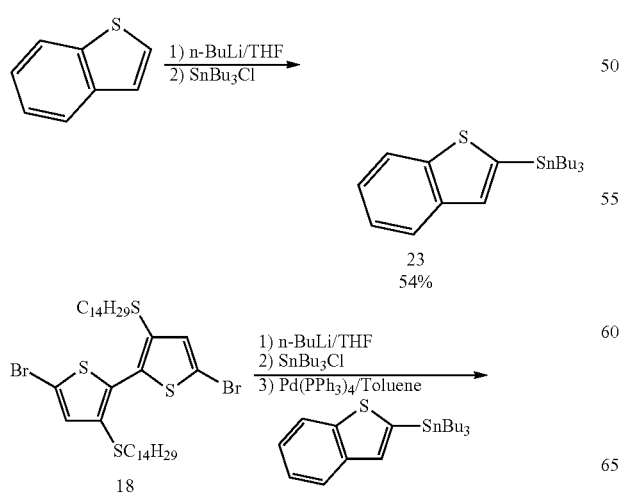

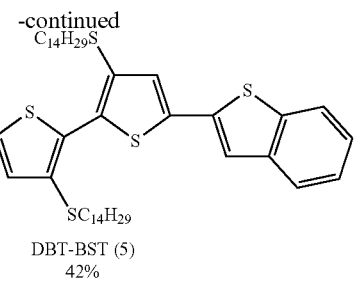

DBT-BST (5)
42%

(1) Synthesis of 2-tributylstannylbenzo[b]thiophene 23

2.5 M of n-BuLi (3.1 mL/hexane, 7.67 mmol) was added to benzo[b]thiophene (1.05 g, 7.67 mmol/THF (20 mL)) and reacted at 0° C. for 1 hour under a dry and anaerobic operation condition to form a solution. SnBu₃Cl (2.38 mL, 8.44 mmol) was then added to the solution and reacted at 0° C. for 30 minutes. After returning to room temperature, the solution was continuously reacted for 8 hours. After the reaction was completed, the solution was extracted by ether (30 mL) and deionized water (50 mL). An organic phase was collected. After removal of ether by a rotary concentrator, the organic phase was purified by reduced-pressure distillation to form a transparent pale yellow oily product (23, 1.76 g, 54%).

(2) Synthesis of 5,5'-di(benzo[b]thiophen-2-yl)-3,3'-bis(tetradecanylsulfanyl)-2,2'-bithiophene (DBT-BST) 5

2-tributylstannylbenzo[b]thiophene 23 (0.25 g, 0.56 mmol) was added to diBr-BST 18 (0.21 g, 0.26 mmol/Pd(PPh₃)₄ (12 mg, 0.01 mmol)/toluene (30 mL)) and reacted with thermal reflux at 140° C. for 2 days under a dry and anaerobic operation condition to form a solution. After the reaction was completed, the solution was spun to remove toluene. The solution was then purified by column chromatography using hexane as an elution solution and recrystallized to obtain an orange solid (5, 100 mg, 42%).

¹H NMR (300 MHz, CDCl₃): 7.78 (dd, J=6.6 Hz, J=1.8 Hz, 4H), 7.45 (s, 2H), 7.34 (m, 4H), 7.27 (s, 2H), 2.89 (t, J=7.2 Hz, 4H), 1.63 (m, 4H), 1.38 (m, 4H), 1.22 (m, 40H), 0.87 (t, J=6.6 Hz, 6H).

Example 4

Synthesis of the Bithiophene Derivative IV
(Compound DBTT-BST)

IV

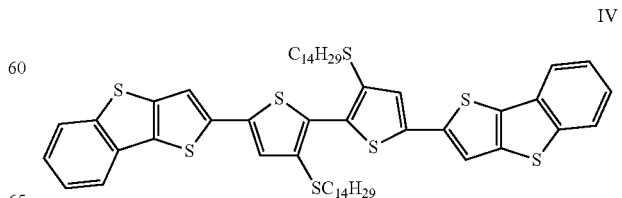

Synthesis Scheme:

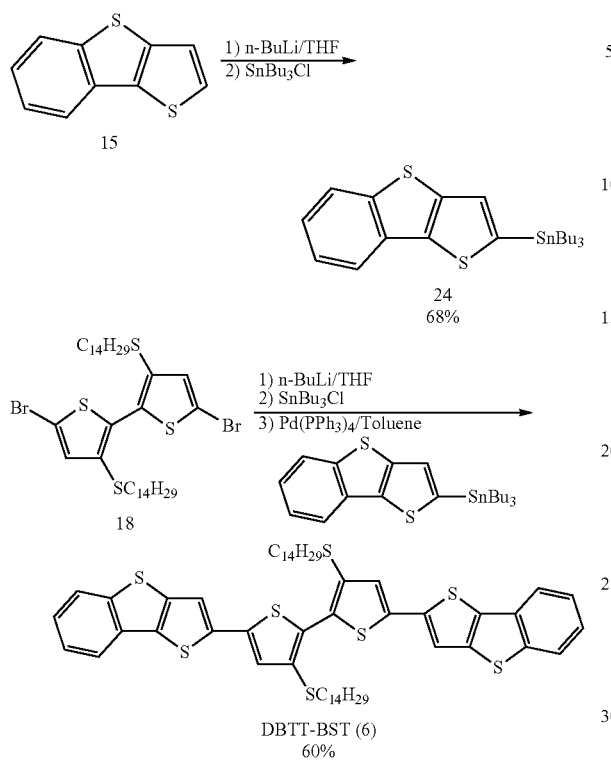

(1) Synthesis of 2-tributylstannylbenzo[d,d']thieno[3,2-b]thiophene 24

2.5 M of n-BuLi (2.2 mL/hexane, 5.57 mmol) was added to benzo[d,d']thieno[3,2-b]thiophene 15 (1.06 g, 5.57 mmol/THF (20 mL)) and reacted at 0° C. for 1 hour under a dry and anaerobic operation condition to form a solution. SnBu$_3$Cl (1.73 mL, 6.13 mmol) was then added to the solution and reacted at 0° C. for 30 minutes. After returning to room temperature, the solution was continuously reacted for 8 hours. After the reaction was completed, the solution was extracted by ether (30 mL) and deionized water (50 mL). An organic phase was collected. After removal of ether by a rotary concentrator, the organic phase was purified by reduced-pressure distillation to form a transparent pale yellow oily product (24, 1.81 g, 68%).

(2) Synthesis of 5,5'-di(benzo[d,d']thieno[3,2-b]thiophen-2-yl)-3,3'-bis(tetradecanylsulfanyl)-2,2'-bithiophene (DBTT-BST) 6

2-tributylstannylbenzo[d,d']thieno[3,2-b]thiophene 24 (0.43 g, 0.88 mmol) was added to diBr-BST 18 (0.31 g, 0.4 mmol/Pd(PPh$_3$)$_4$ (18.5 mg, 0.02 mmol)/toluene (30 mL)) and reacted with thermal reflux at 140° C. for 2 days under a dry and anaerobic operation condition to form a solution. After the reaction was completed, the solution was spun to remove toluene. The solution was then purified by column chromatography using toluene as an elution solution and recrystallized to obtain a red solid (6, 241 mg, 60%).

$^1$H NMR (300 MHz, CDCl$_3$): δ 7.86-7.80 (q, J=7.5, 4H), 7.45 (s, 2H), 7.43-7.33 (m, 4H), 7.25 (s, 2H), 2.90 (t, J=7.2 Hz, 4H), 1.64 (m, 4H), 1.38, (m, 4H), 1.21 (m, 40H), 0.86 (t, J=6.6 Hz, 6H).

Example 5

Synthesis of the Bithiophene Derivative V (Compound DDTT-BST)

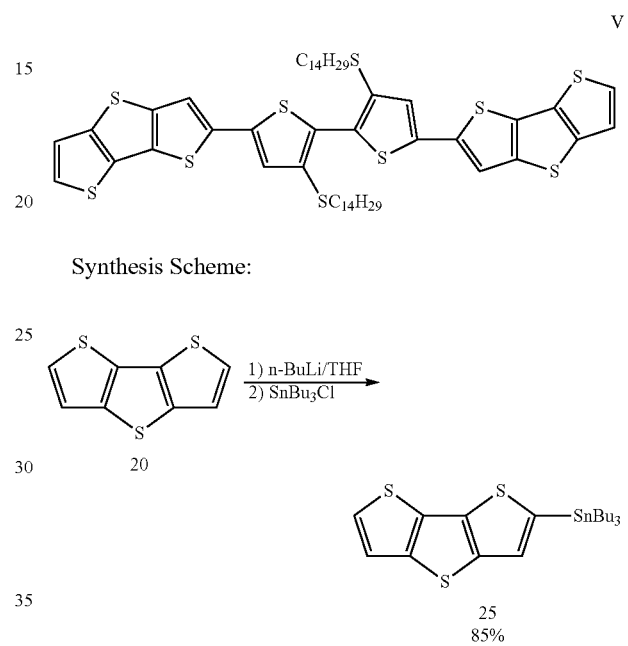

Synthesis Scheme:

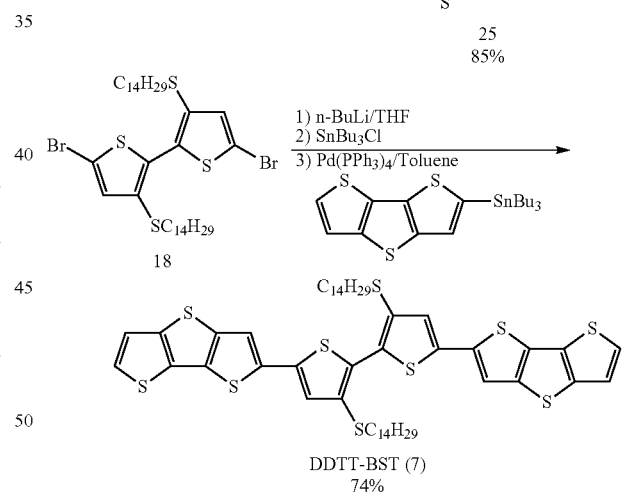

(1) Synthesis of 2-tributylstannyldithieno[3,2-b;2',3'-d]thiophene 25

2.5 M of n-BuLi (2.04 mL/hexane, 5.09 mmol) was added to dithieno[3,2-b;2',3'-d]thiophene 20 (1 g, 5.09 mmol/THF (20 mL)) and reacted at 0° C. for 1 hour under a dry and anaerobic operation condition to form a solution. SnBu$_3$Cl (1.58 mL, 5.6 mmol) was then added to the solution and reacted at 0° C. for 30 minutes. After returning to room temperature, the solution was continuously reacted for 8 hours. After the reaction was completed, the solution was extracted by ether (30 mL) and deionized water (50 mL). An organic phase was collected. After removal of ether by a rotary concentrator, the organic phase was purified by reduced-pressure distillation to form a transparent pale yellow oily product (25, 2.1 g, 85%).

(2) Synthesis of 5,5'-di(dithieno[3,2-b;2',3'-d]thiophen-2-yl)-3,3'-bis(tetradecanylsulfanyl)-2,2'-bithiophene (DDTT-BST) 7

2-tributylstannyldithieno[3,2-b;2',3'-d]thiophene 25 (0.34 g, 0.7 mmol) was added to diBr-BST 18 (0.25 g, 0.32 mmol/Pd(PPh$_3$)$_4$ (14.7 mg, 0.01 mmol)/toluene (30 mL)) and reacted with thermal reflux at 140° C. for 2 days under a dry and anaerobic operation condition to form a solution. After the reaction was completed, the solution was spun to remove toluene. The solution was then purified by column chromatography using toluene as an elution solution and recrystallized to obtain a red solid (7, 237 mg, 74%).

$^1$H NMR (300 MHz, CDCl$_3$): 7.42 (s, 2H), 7.39 (d, J=5.1, 2H), 7.29 (t, J=5.1, 2H), 7.19 (s, 2H), 2.29 (t, J=7.5 Hz, 4H), 1.63 (m, 4H), 1.37 (m, 4H), 1.21 (m, 40H), 0.86 (t, J=7.2 Hz, 6H).

Example 6

Synthesis of the Bithiophene Derivative VI (Compound DBTDT-BST)

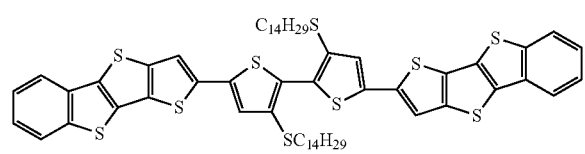
VI

Synthesis Scheme:

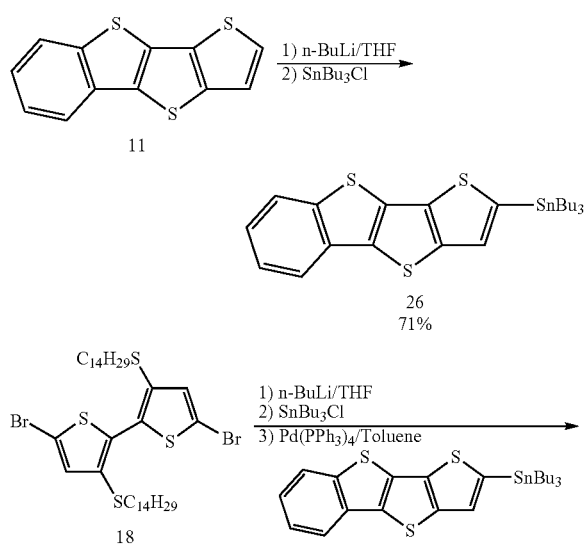

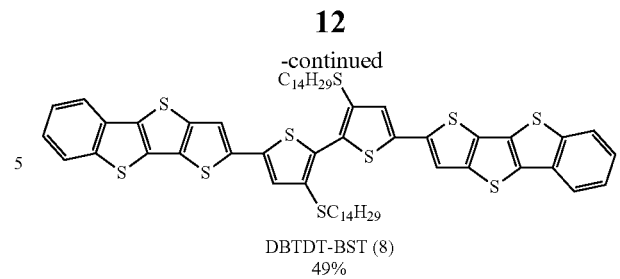
DBTDT-BST (8)
49%

(1) Synthesis of 2-tributylstannylbenzo[d,d']thieno[3,2-b;4,5-b']dithiophene 26

2.5 M of n-BuLi (1.87 mL/hexane, 4.69 mmol) was added to benzo[d,d']thieno[3,2-b;4,5-b']dithiophene 11 (1.1 g, 4.46 mmol/THF (20 mL)) and reacted at 0° C. for 1 hour under a dry and anaerobic operation condition to form a solution. SnBu$_3$Cl (1.38 mL, 4.9 mmol) was then added to the solution and reacted at 0° C. for 30 minutes. After returning to room temperature, the solution was continuously reacted for 8 hours. After the reaction was completed, the solution was extracted by ether (30 mL) and deionized water (50 mL). An organic phase was collected. After removal of ether by a rotary concentrator, the organic phase was purified by reduced-pressure distillation to form a transparent pale yellow oily product (26, 1.7 g, 71%).

(2) Synthesis of 5,5'-di(benzo[d,d']thieno[3,2-b;4,5-b']dithiophen-2-yl)-3,3'-bis(tetradecanylsulfanyl)-2,2'-bithiophene (DBTDT-BST) 8

2-tributylstannylbenzo[d,d']thieno[3,2-b']dithiophene 26 (0.31 g, 0.57 mmol) was added to diBr-BST 18 (0.2 g, 0.26 mmol/Pd(PPh$_3$)$_4$ (12 mg, 0.01 mmol)/toluene (30 mL)) and reacted with thermal reflux at 140° C. for 2 days under a dry and anaerobic operation condition to form a solution. After the reaction was completed, the solution was spun to remove toluene. The solution was then purified by column chromatography using toluene as an elution solution and recrystallized to obtain a red solid (8, 142 mg, 49%).

$^1$H NMR (500 MHz, CDCl$_3$): δ 7.88-7.81 (q, J=7.5, 4H), 7.48 (s, 2H), 7.44 (t, J=7.5, 2H), 7.36 (t, J=7.5, 2H), 7.19 (s, 2H), 2.91 (t, J=7.5 Hz, 4H), 1.67 (m, 4H), 1.46 (m, 4H), 1.24 (m, 40H), 0.87 (t, J=6.5 Hz, 6H).

Example 7

Physical Properties of the Bithiophene Derivatives

The crystallization characteristics of the bithiophene derivatives I-VI were analyzed by XRD. The results are shown in Table 1.

TABLE 1

| Bithiophene derivatives | 2θ (°) | Intensity (a.u.) |
|---|---|---|
| I | 4.70 | 361 |
| II | 5.76 | 998 |
| III | 5.85 | 800 |
| IV | 5.61 | 1262 |
| V | 6.16 | 1850 |
| VI | 5.43 | 1401 |

In accordance with the XRD analysis results, the bithiophene derivatives I-VI possessed high crystallization characteristics, resulting in improved electrical performance.

Example 8

Performance Test of the Semiconductor Devices

Referring to FIG. 1, in the semiconductor device 10, the gate electrode 14 was ITO. The insulation layer 16 was silicon dioxide. The semiconductor layer 22 comprised the bithiophene derivatives I-VI. The material of the source 18 and the drain 20 were gold.

The electrical performance (when $V_D$=-50V), carrier mobility and Vth value of the semiconductor devices I-VI fabricated by the semiconductor layer comprising the bithiophene derivatives I-VI are respectively shown in FIGS. 2-7 ($I_D$-$V_G$ figures) and Table 2.

TABLE 2

| Semiconductor devices | Carrier mobility (cm²/V-sec) | Vth value (V) |
|---|---|---|
| I | 0.006 | 5.3 |
| II | 0.05 | -2.2 |
| III | 0.18 | -8.4 |
| IV | 0.21 | 2.3 |
| V | 0.32 | -1.2 |
| VI | 0.45 | -2 |

In accordance with Table 2, the present semiconductor devices possessed improved carrier mobility and Vth value. In particular, when bithiophene derivative VI was used as the semiconductor layer, the semiconductor device had carrier mobility of up to 0.45 cm²/V-sec.

While the disclosure has been described by way of example and in terms of preferred embodiment, it is to be understood that the disclosure is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A bithiophene derivative of formula (I):

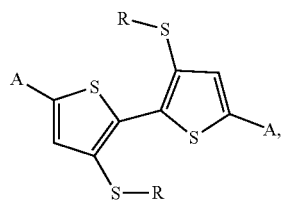

(I)

wherein
R is C8-25 alkyl; and
A is selected from

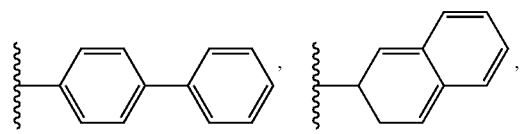

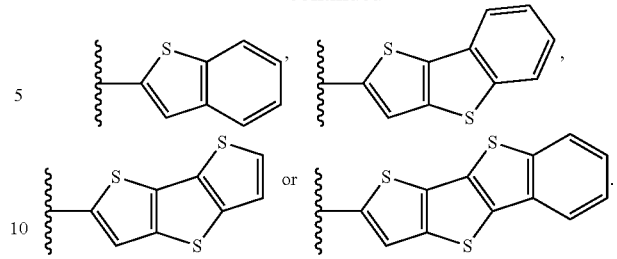

2. The bithiophene derivative as claimed in claim 1, wherein the bithiophene derivative is

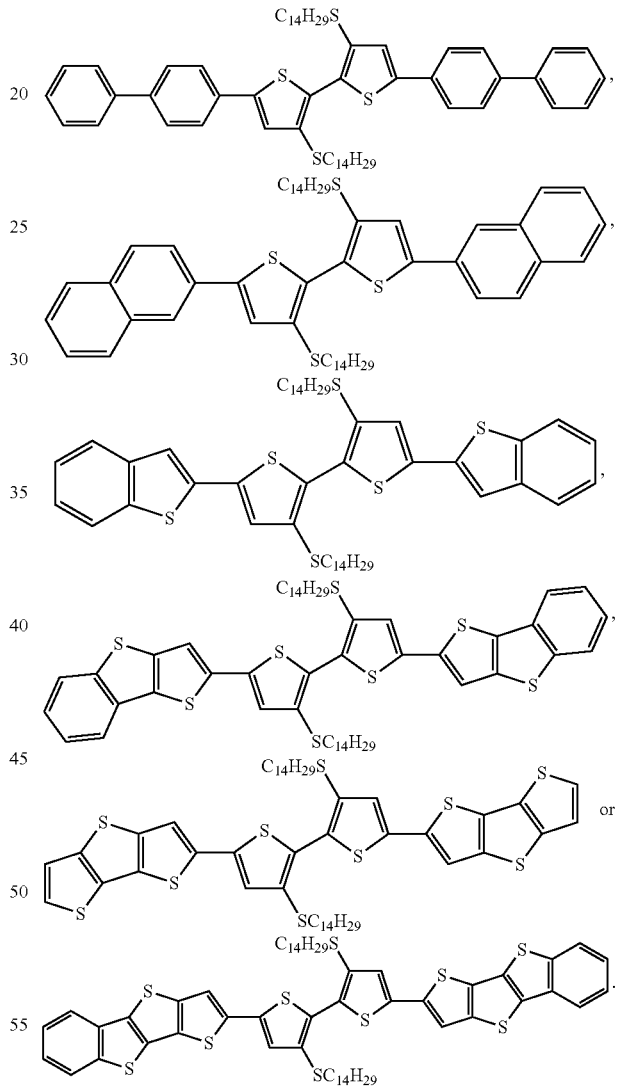

3. A semiconductor device, comprising:
   a substrate;
   a gate electrode formed on the substrate;
   an insulation layer formed on the gate electrode and the substrate;
   a source and a drain formed on the insulation layer; and
   a semiconductor layer formed on the insulation layer, the source and the drain, wherein the semiconductor layer comprises the bithiophene derivative as claimed in claim 1.

4. The semiconductor device as claimed in claim 3, wherein the substrate comprises glass substrate, quartz substrate, silicon wafer, plastic substrate or metal film.

5. The semiconductor device as claimed in claim 3, wherein the gate electrode, the source and the drain comprise metal or conductive polymers.

* * * * *